(12) United States Patent
Chan et al.

(10) Patent No.: US 6,740,756 B1
(45) Date of Patent: May 25, 2004

(54) FLUORESCENT LANTHANIDE CHELATES

(75) Inventors: George Wai-Kin Chan, Wynnewood, PA (US); Robert P. Hertzberg, Downington, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/720,965

(22) PCT Filed: Jul. 7, 1999

(86) PCT No.: PCT/US99/15366
§ 371 (c)(1),
(2), (4) Date: Jun. 20, 2001

Related U.S. Application Data

(60) Provisional application No. 60/091,949, filed on Jul. 7, 1998.

(51) Int. Cl.[7] .................. C07D 491/00; C07D 211/68; C07D 311/82; C07C 229/00; G01N 21/76
(52) U.S. Cl. ............... 546/89; 546/194; 549/393; 552/236; 552/238; 562/565; 436/172; 206/569
(58) Field of Search ................ 562/565; 546/39, 546/86, 194; 549/393; 552/236, 238; 436/172; 206/569

(56) References Cited

U.S. PATENT DOCUMENTS

| | | | |
|---|---|---|---|
| 4,824,986 A | * | 4/1989 | Gansow |
| 5,162,508 A | | 11/1992 | Lehn et al. |
| 6,410,695 B1 | | 6/2002 | Sinn et al. |

FOREIGN PATENT DOCUMENTS

| | | |
|---|---|---|
| DE | 195 05 960 | 8/1996 |
| WO | WO 96 00901 | 1/1996 |
| WO | WO 99 66780 | 12/1999 |

OTHER PUBLICATIONS

Bozhevol'nov et al Zh. Anal. Khim., Determination of Organic Substances by Sensitized Luminence of Rare Earths, 1979, 34(2) pp. 344–347.*
Bailey, M. Philip, et al. Analyst, vol. 110, 1985, pp. 603–604, XP001040544.
Chemcial Abstracts Service, Database accession No. 127:77478/DN, HCAPLUS XP002219212, abstract, RN191661–01–5, & Ozaki, H. et al.: Kidorui, vol. 30, 1997, pp. 358–359.

Gong, et al., "Stability constants and fluorescence of terbium (III) complexes with polyaminopolycarboxylates in aqueous solution", (1998), Chem. Res. Chin. Univ., 14(4), pp. 359–364 (abstract), Database CAPLUS on STN, Acc. No. 1999:130288.
Chen, et al., "Thiol–reactive luminescent chelates of terbium and europium", (1999), Bioconjugate Chem., 10(2), pp. 311–315 (abstract), Database CAPLUS on STN, Acc. No.: 1999: 79347.
Gong, et al., "Synthesis of new polyaminopolycarboxylic acid (STPA.2pAS) and fluorescence of its TB3+ complexes in aqueous solution", (1997), Zhonguo Xitu Xuebao, 15(4), pp. 289–294 (abstract), Database CAPLUS on STN, Acc. No. 1998: 800284.
Phimphivong, et al, "Terbium chelate membrane label for time–resolved, total internal reflection fluorescence microscopy of substrate–adherent cells", (1998), Bioconjugate Chem., 9(3), pp. 350–357 (abstract), Database CAPLUS on STN, Acc. No. 1999: 269349.
Li, et al., "Amine–reactive forms of a luminescent diethylenetriaminepentaacetic acid chelate of terbium and europium: attachment to DNA and ergy transfer measurements", (1997), Bioconjugate Chem., 8(2), pp. 127–132 (abstract), Database CAPLUS on STN, Acc. No. 1999: 154993.

* cited by examiner

*Primary Examiner*—Paul A. Zucker
(74) *Attorney, Agent, or Firm*—Loretta J. Henderson; Charles M. Kinzig

(57) ABSTRACT

The present invention provides complexing agents of Formula I

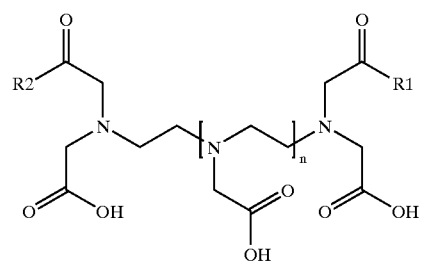

which contain novel photosensitizers and produce long-lived fluorescence for use in bioaffinity assays, especially HTRF (homogeneous time-resolved fluorescence) assays.

19 Claims, No Drawings

FLUORESCENT LANTHANIDE CHELATES

This application is a 371 of PCT/US99/15366 filed Jul. 7, 1999 which claims benefit of provisional No. 60/091,944 filed Jul. 7, 1998.

FIELD OF INVENTION

The present invention relates to the identification and preparation of organic agents that can complex lanthanide cations. In particular, this invention relates to complexing agents which contain novel photosensitizers and can produce long-lived fluorescence for use in bioaffinity assays, especially HTRF (homogeneous time-resolved fluorescence) assays.

BACKGROUND OF THE INVENTION

A wide variety of bioassays are used in the pharmaceutical industry to identify drug development candidate compounds. Recent advances in the identification of pharmaceutical targets, together with the vastly increased output of new compounds using techniques such as combinatorial chemistry have created a need to increase bioassay throughput (number of samples measured per unit time) drastically to meet discovery objectives. Robotics, miniaturization and homogeneous assay formats have all been incorporated into high throughput screening (HTS) assays to increase throughput. Ideally, an analytical technique suitable for both miniaturization and homogeneous assay formats must provide maximal detection sensitivity and interaction in situ, while requiring only minimal assay time and liquid handling (e.g., separation and filtration). Present analytical techniques, such as those which use radiolabels, are unsatisfactory for HTS use because they lack sensitivity, require large sample size and manual liquid handling.

Compared to traditional radiolabels, fluorescent labels have more desirable lifetime, solubility and sensitivity properties for use in HTS assays. The unique lifetime properties of fluorescent labels also meet the needs of fluorescence polarization (FP) and fluorescence correlation spectroscopy (FCS) in the investigation of slow rotational and translational changes in macromolecules.

Traditional fluorescent labels such as organic dyes, e.g., fluoresceins and rhodamines, have long been employed as bioanalytical tools in immunoassays. More recently, lanthanide chelates have been developed as fluorescence agents for use in the bioassay field. These lanthanide chelates have been reviewed. See Dickson, J. *Photochemistry and Photobiology*, 27(1995) 3–9; and Mathis, J. *Clinical Ligand Assay* 20 (1997) 141–145.

The lanthanide chelates are capable of producing long-lived and long wavelength fluorescent emissions upon excitation. In time-delay measurements, they have demonstrated clear advantages over conventional fluorescent labels, in particular less quenching and background interference, while exhibiting increased detection sensitivity. In addition to these advantages, many lanthanide chelates have demonstrated superior solubility properties and are able to efficiently transfer energy from their excited states to neighboring acceptor molecules. These advantages render lanthanide chelates ideal agents for HTRF use, especially for developing high-throughput automated and miniaturized binding assays, inncluding immunoassays, DNA hybridization assays, receptor binding assays, enzyme assays, cell-based assays, immunocytochemcial or immunohistochemical assays.

A number of lanthanide (e.g. terbium, europium) complexes are known, but only three classes of lanthanide chelates, exemplified by the compounds shown in Table I below, are considered to be useful in HTRF:

TABLE I

Cryptates (Packard) bipyridine type; i.e.

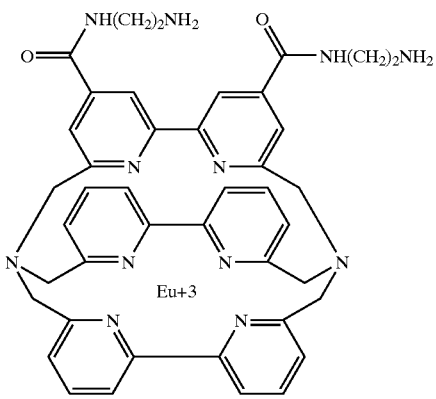

DTPA Chelates (Berkeley) diethylenetriamine-pentaacetic acid type; i.e.

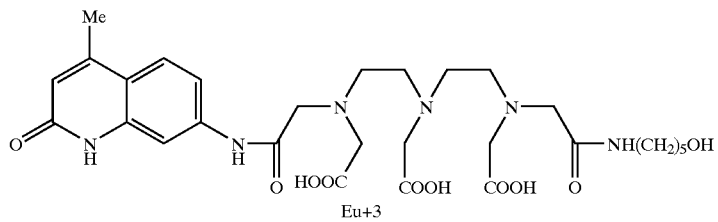

TABLE I-continued

| PMDA Chelates (Wallac) pyridylmethylamine-diacetic acid type; i.e. | 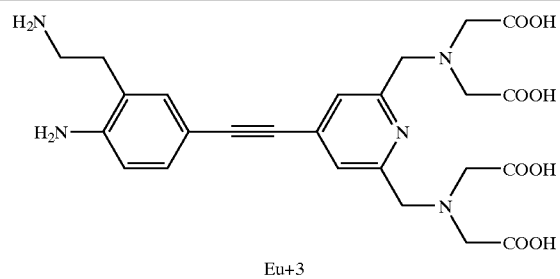 |
|---|---|
| | Eu+3 |

These chelates haven been described as having chemical stability, long-lived fluorescence (greater than 0.1 ms lifetime) after bioconjugation and significant energy-transfer in specific bioaffinity assay U.S. Pat. No. 5,162,508, issued to Lehn, et al. on Nov. 10, 1992 discloses bipyridine cryptates. Polycarboxylate chelators with TEKES type photosensitizers (EP 0203047 A1) and terpyridine type photosensitizers (EP 0649020 A1) are known. International Publication No. WO 96/00901 of Selvin et al., having an International Publication Date of Jan. 11, 1996, discloses diethylenetriaminepentaacetic acid (DTPA) chelates winch used carbostyril as sensitizer. Baley, et al., *Analyst*, 109, (1984) 1449; Ando, et al. *Biochim. Biophys. Acta*, 1102, (1992) 186; and Heyduk et al., *Anal. Biochemistry*, 248, (1997) 216 also describe DTPA lanthanide chelates which contain different sensitizers. Additional DTPA chelates with other sensitizers and other tracer metal are known for diagnostic or imaging use (e.g., EP 0450742 A1).

The lanthanide chelates provided by the present invention include novel sensitizers which differ from carbostyril and other known chelates. More specifically, these novel sensitizers impart onto the present chelates advantageous physicochemical properties pertaining to excitation wavelength, lifetime, quantum yield, quenching effect, complex stability, photostability, solubility, charge, nonspecific protein interaction, biocoupling efficiency and ease of preparation. Such advantages are desirable to provide a diversity of novel fluorescent probes for use in, and development of, HTRF assays.

SUMMARY OF THE INVENTION

An object of the present invention is to provide novel lanthanide chelate compounds, and a method for using such compounds in fluorescence detection-based techniques or bioassays.

Accordingly, in the first aspect, this invention provides a compound according to Formula I.

In still another aspect, this invention provides a method for using the compounds of Formula I in fluorescence detection-based techniques or bioassays.

In yet another aspect, this invention provides a kit for fluorescence detection-based techniques or bioassays which use the compounds of Formula I as the basis for signal detection and measurement.

DETAILED DESCRIPTION OF THE INVENTION

Each compound of the present invention comprises four functional parts: a lanthanide metal cation (e.g. Tb III, Eu III, Sm III, Dy III), a chelator for the lanthanide metal, a photosensitizer for photoexcitation and energy transfer, and a linker for bioconjugation to the target biomolecule, that is, the biomolecule being measured using a fluorescence detection-based spectroscopic technique or bioassay.

The present invention provides compounds of Formula I:

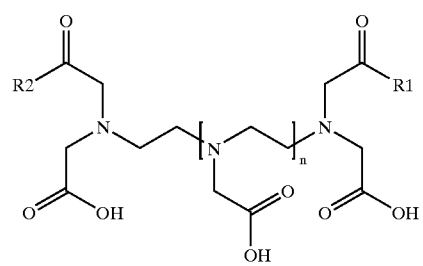

wherein:

$[\text{NA}]_n$ is a chelator selected from the group consisting of: diethylenetriaminepentaacetic acid (DTPA) (n=1) or triethylenetetraaminehexaacetic acid (TTHA) (n=2) or a polyaminocarboxylate derivative of DTPA or TTHA, preferably DTPA, which chelates a lanthanide metal cation, preferably selected from the group consisting of: Tb III, Eu III, Sm III, and Dy III.

The sensitizer R1 is usually related to an aromatic or heteroaromatic amine whose chromophore plays a vital role in excitation and energy transfer. Superior sensitizers usually have highly conjugated systems and an added capacity for lanthanide complexation. We have found several sensitizers, belonging to two structural classes—phenones and quinolines—that provide highly fluorescent compounds of Formula I. R1 is more preferably selected from the following group: aminoacetophenones (AAP), aminobenzophenones (ABP), aminofluorenones (AF), aminoxantones (AX), amino-azaxanthones (AAX), aminoanthraquinones (AAQ), and aminoacridones (AAC):

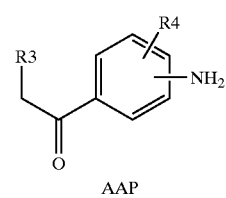

AAP

-continued

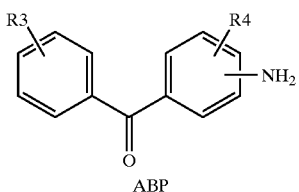
ABP

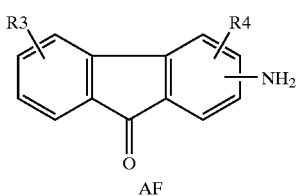
AF

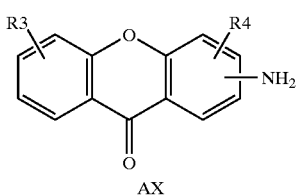
AX

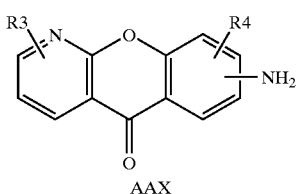
AAX

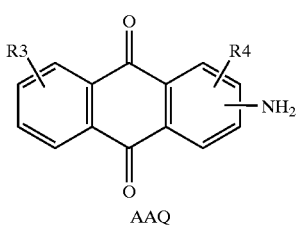
AAQ

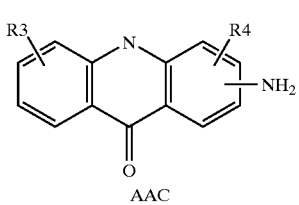
AAC wherein for each nucleus, the amino group $NH_2$ may be attached at one of any possible positions on the phenyl ring. The point of amide attachment to the chelator $[\backslash NA]_n$ in Formula I may similarly be attached at one of any possible positions on the phenyl ring. R3 and R4 are independently selected from the group consisting of: H, OH, $NH_2$, $COCH_3$, COPh, OPh, NHPh, CN, $NO_2$, $CO_2H$, $CO_2CH_3$, I, Br and Cl.

Sensitizers of the present invention belonging to the quinoline class can be further categorized into 3-aminoquinolines (3AQ), and 6-aminoquinolines (6AQ). Preferably in the quinoline compounds of the present invention, R1 is selected from the group consisting of:

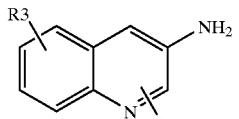
3AQ

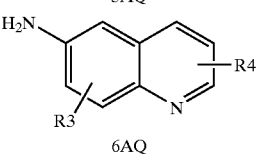
6AQ wherein R3 and R4 are as defined herein above.

The linker R2 is an amine or other moiety having a functional group that can bioconjugate or can be derivatized to couple with biomolecules. In a preferred embodiment of the present invention, R2 is selected from the group consisting of: OH, $NH(CH_2)_nOH$, $NH(CH_2)_nNH_2$, $NH(CH_2)_nPhNH_2$, $NH(CH_2)_nPhOH$, $NHCH(CO_2H)CH_2PhNH_2$, $NH(CH_2)_nPhNCS$; wherein n is 1–12. The present invention also contemplates the use of other linkers known in the art for coupling.

Particularly preferred compounds of the present invention include the DTPA chelates listed in Table II below:

TABLE II

| | | | Lifetime, msec Lanthanide | |
|---|---|---|---|---|
| Formula | R1 | R2 | Eu | Tb |
| I | 3AAP | — | 0.59 | 1.73 |
| I | 3AQ | — | 0.59 | |
| I | 6AQ | — | 0.60 | |
| I | 4ABP | — | 0.60 | 1.03 |
| I | 3AAP | 4APEA | 0.50 | 1.62 |
| I | 3AAP | 4APEA-ITC | 0.62 | 1.65 |
| I | 3AAP | 4APA | 0.60 | 1.70 |
| I | 3AQ | 4APEA | | |
| I | 3AQ | CAD | | |
| I | 6AQ | 4APEA | | |
| I | 6AQ | CAD | 0.58 | |
| I | 4ABP | 4APEA | 0.43 | 0.73 |
| I | 4ABP | CAD | 0.59 | 0.82 |

Abbreviations:
3AAP: 4-aminoacetophenone
3AQ: 3-aminoquinoline
6AQ: 6-aminoquinoline
4ABP: 4-aminobenzophenone
4APEA: 4-aminophenethylamine
4APEA-ITC: 4-isothiocyanatophenethylamine
4APA: 4-aminophenylalanine
DTPA: Diethylene-triamine-pentaacetic acid
TTHA: Triethylene-tetramine-hexaacetic acid
CAD: Cadaverine or 1,5-diaminopentane More particularly preferred compounds of the present invention include the DTPA chelates below:

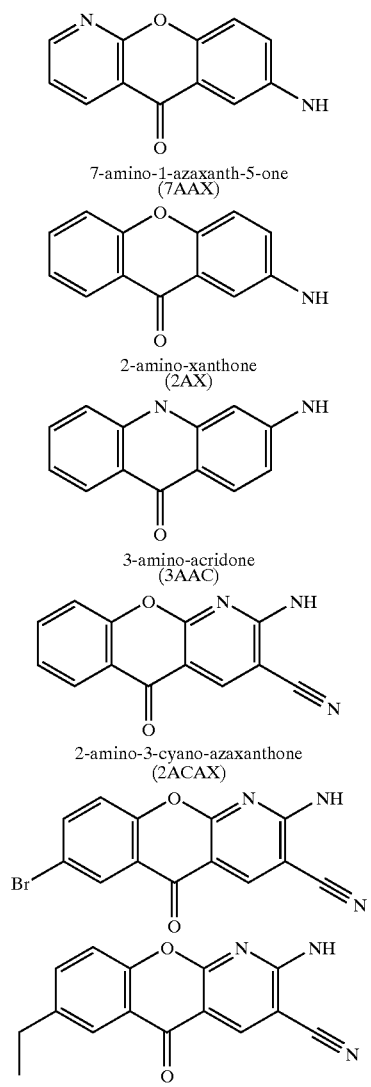

2-amino-3-cyano-7-bromo-azaxanthone2-amino-3-cyano-7-ethyl-azaxanthone (2ACBAX)(2ACEAX)

Definitions

Sensitizer and chelator moiety abbreviations are as defined in Table II above.

The terms "bioconjugate" and "bioconjugatable" mean the ability of a functional group or groups on a chemical moiety to form covalent linkage to biomolecules.

The term "polycarboxylate derivative of DTPA or TTHA" means a compound which differs from DTPA and TTHA by changing the length of N-acetic acid units, or by rearranging the units from a linear to a cyclic form.

The term "bioassay" means immunoassays, DNA hybridization assays, receptor binding assays, enzyme assays, cell-based assays, immunocytochemcial or immunohistochemical assays and the like.

Method of Preparation

The sensitizers and space linkers with structures described herein above are employed in a manner shown in Scheme I and in the Examples. The first step in the synthetic route involves reacting the sensitizer amine, hereby exemplified by 3-aminoacetophenone, with equal or higher molar ratio of DTPAA (diethylene-triamine-pentaacetic anhydride) in the presence of triethylamine. The product formed is not isolated but allowed to react with an equal or a slight molar excess of the linker amine, hereby exemplified by 4-aminophenethylamine. The disubstituted derivative is then isolated and purified by HPLC before converting the linker amino group into a bioconjugatable function. The final step is to react the product (Compound 5) with thiophosgene in a slightly acidic condition to form the isothiocyanate (Compound 6). Alternatively, a chlorotirazine derivative instead of an isothiocyanate can also be prepared from Compound 5 for facile labelling of target molecules with a reactive amino function.

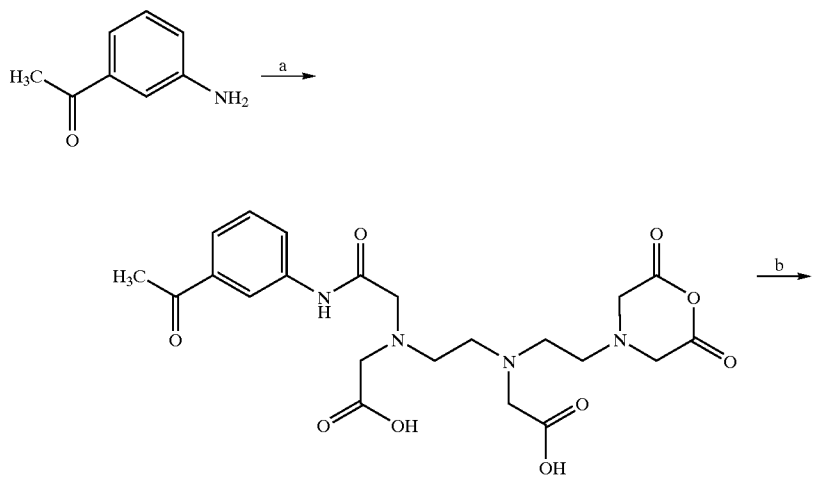

-continued

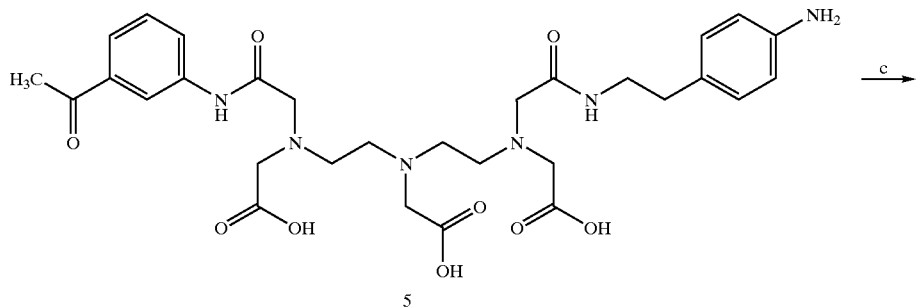

5

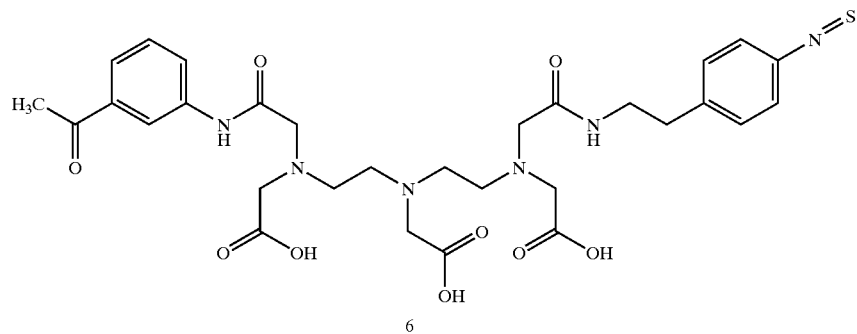

6 a) DTPAA, DMSO, Et₃N; b) 4APEA, DMSO, Et₃N; c) CSCl₂, MeCl₂—H₂O

Utility of the Invention

The compounds of this invention can be used for labelling donor peptides, proteins, DNAs, enzyme substrates, ligand molecules in immunoassays, DNA hybridization assays, receptor binding assays, enzyme assays, cell-based assays, immunocytochemcial or immunohistochemical assays and the like. These bioassays can be also formated for ultrasensitive high-throughput screening assays. In the bioassay, the lanthanide chelate is excited in a fluorescence instrument and provide energy transfer to an acceptor molecule such as an organic dye (e.g. allophycocyanin (APC), or indodicarbocyanin or CY-5) capable of providing the desired long-lived fluorescense emission for quantitation.

The present invention also provides a method for using the compounds of Formula I in fluorescence detection-based techniques or bioassays. The present method comprises the steps of:

1. labelling an aliquot comprising donor biomolecules selected from the group consisting of: peptides, proteins, deoxyribonucleic acids (DNAs), ribonucleic acids (RNAs), enzyme substrates, and ligand molecules with a compound of Formula I by a linking reaction with linker R2 to provide a labelled biomolecule assay sample;
2. adding a suitable amount of a suitable organic dye, preferably selected from the group consisting of: allophycocyanin (APC) and indodicarbocyanin (CY-5), to the labelled biomolecule assay sample;
3. exciting the labelled biomolecule assay sample in a suitable fluorescence instrument to provide a fluorescense emission for quantitation.

Fluorescence instruments suitable for use, in the inventive method include the Photon Technology International, Model LS-100, Luminescence System.

The present invention further provides a kit for fluorescence detection-based techniques or bioassays which use the compounds of Formula I as the basis for signal detection and measurement, such kit comprising:

1. a suitable amount of a compound of Formula I; and
2. a suitable amount of organic dye, preferably selected from the group consisting of: allophycocyanin (APC), indodicarbocyanin (CY-5) and rhodamine. Such a kit provides instructions for proper use thereof, including the appropriate amounts of the compound of Formula I and the organic dye to use for a particular bioassay sample molecular type and size.

General

Proton NMR spectra were recorded at 400 MHz using a Bruker AMX 400 spectrometer. CDC13 is deuteriochloroform, DMSO-d₆ is hexadeuteriodimethylsulfoxide, and) CD₃OD is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Fourier transform infrared (FTIR) spectra were recorded on a Nicolet Impact 400 D infrared spectrometer. IR and FTIR spectra were recorded in transmission mode, and band positions are reported in inverse wavenumbers (cm⁻¹). Mass spectra were taken on either VG 70 FE, PE Syx API III, or VG ZAB HF instruments, using fast atom bombardment (FAB) or electrospray (ES) ionization techniques.

EXAMPLES

In the following synthetic examples, temperature is in degrees Centigrade (° C.). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Referring to Table II and the Method of Preparation section:

Example 1

Preparation of 3AAP-DTPA (1) and 3AAP-DTPA-4APEA (5)

To solution of DTPA (143 mg, 0.4 mmol) in 10 mL dry DMSO and 2 mL dry triethylamine was added a solution of 3-aminoacetophenone (3AAP, 54 mg, 0.4 mmol) in 5 mL DMSO. The mixture was stirred at room temperature for 0.5 h and then treated with a solution of 4-aminophenethylamine (4APEA, 53 mg, 0.4 mmol) in 5 mL DMSO. The mixture was allowed to stir at room temperature for an additional 3 h and then evaporated dryness. The oily residue was chromatographed on reversed-phase C18 hplc (using a step gradient of 0 to 60% acetonitrile in 0.1% TFA buffer) to give, after lyophilization, 1 as a cream colored solid and 5 as a pale yellow solid. Compound 1 was obtained in 59 mg yield. $^1$H-NMR (CD$_3$OD): d 2.60 (3H, s), 3.1–3.5 (10H, m), 3.6 (2H, s), 3.65 (2H, s), 3.71 (2H, s), 4.42 (2H, s), 7.42 (1H, dd), 7.75 (1H, dd), 7.83; (1H, dd), 8.31 (1H, d); MS: m/z 511 (M-H), Compound 5 was obtained in 16 mg, yield. $^1$H-NMR (CD3OD): d 2.62 (3H, s), 2.73 (2H, t), 3.21 (2H, t), 3.3–3.55 (12H, m), 3.65 (2H, s), 3.74 (2H, s), 4.35 (2H, s), 7.13 (4H, s), 7.41 (1H, dd), 7.75 (1H, dd), 7.83 (1H, dd), 8.32 (1H,d); MS: m/z 682 (M+3NH$_4$), 683 (MH+3NH$_4$).

Example 2

Preparation of 4AAP-DTPA-APEA-ITC (6).

To a solution of 4AAP-DTPA-APEA (3, 12 mg, 0.019 mmol) in 10 mL of 0.5 N HCl was added 4 mL of thiophosgene (85% in CCl$_4$). The two phase reaction was allowed to stirred vigorously for 1 h. The mixture was worked up by separating the layers in a separatory funnel and the aqueous solution was washed by additional methylene chloride and then chromatographed on a small reversed-phase C18 column to give the thioisocyanate product (6), an off-white solid in 10 mg yield after lyophilization. $^1$H-NMR (CD$_3$OD): 2.60 (3H, s), 2.72 (2H, t), 3.20 (2H, t), 3.3–3.5 (12H, m), 3.65 (2H, s), 3.74 (2H, s), 4.34 (2H, s), 7.12 (4H, s), 7.41 (1H, ss), 7.74 (1H, dd), 7.84 (1H, dd), 8.20 (1H,d); MS: m/z 724 (M+3NH$_4$), 725 (MH+3NH$_4$); IR: 2108 cm$^{-1}$ (S=C=N stretch).

Example 3

Preparation of 4ABP-DTPA (4) and 4ABP-DTPA-4APEA (12)

To a solution of DTPA (179 mg, 0.5 mmol) in 5 mL of dry DMSO and 3 mL of dry triethylamine was added a solution of 4-aminobenzophenone (4ABP, 99 mg, 0.5 mmol) in 5 mL DMSO. The mixture was stirred for 0.5 h and treated with a solution of 4-aminophenethylamine (4APEA, 68 mg, 0.05 mmol) in 5 mL DMSO. After an additional 3 h stirring at room temperature, the mixture was evaporated to dryness. The oily residue was chromatographed on reversed-phase C18 hplc (using a step gradietn of 0–60% acetonitrile in 0.1% TFA buffer) to give 4 as a cream colored solid and 12 as a pale yellow solid. Compound 4 was obtained in 57 mg yield. $^1$H-NMR (CD$_3$OD): d 3.2–3.5 (10H, m), 3.60 (2H, s), 3.63 (2H, s), 3.74 (2H, s), 4.43 (2H, s), 7.53 (2H, m), 7.62 (1H, dd), 7.76 (2H, m), 7.8 (4H, s); MS: m/z 573 (M+H). Compound 12 was obtained in 47 mg yield. $^1$H-NMR (CD$_3$OD): d 2.73 (2H, t), 3.25 (2H, t), 3.3–3.5 (12H, m), 3.67 (2H, s), 3.73 (2H, s), 4.3 (2H, s), 7.23 (4H, s), 7.55 (2H, m) 7.64 (1H, dd), 7.8 (2H, m), 7.83 (4H, m); MS: m/z 691 (M+H).

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

We claim:
1. A compound of Formula I:

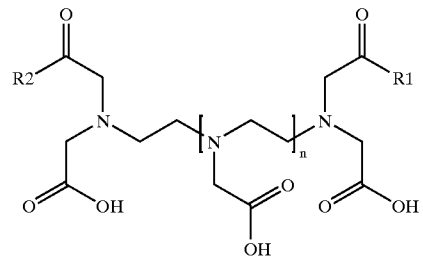

wherein:

[\NΛ]$_n$ is a chelator selected from the group consisting of: diethylenetriaminepentaacetic acid (DTPA), wherein n=1 in Formula I, triethylenetetraaminehexaacetic acid (TTHA), wherein n–2 in Formula I, and a polycarboxylate derivative of DTPA or TTHA, which chelates a lanthanide metal cation;

R1 is a phenone selected from the following group;

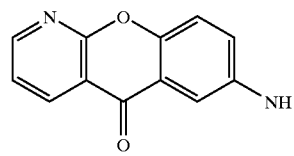

7AAX

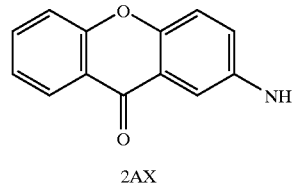

2AX

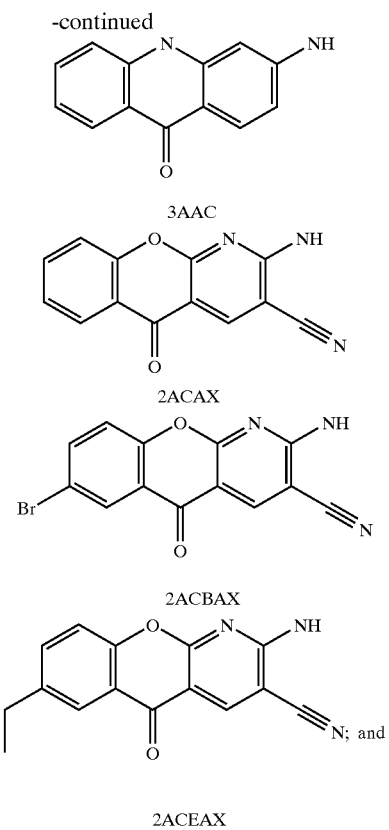

3AAC

2ACAX

2ACBAX

2ACEAX wherein:

R2 is selected from the group consisting of: OH, $NH(CH_2)_nOH$, $NH(CH_2)_nNH_2$, $NH(CH_2)_nPhNH_2$, $NH(CH_2)_nPhOH$, $NHCH(CO_2H)CH_2PhNH_2$, $NH(CH_2)_nPhNCS$; wherein n is 1–6.

2. A method for using a compound of Formula I:

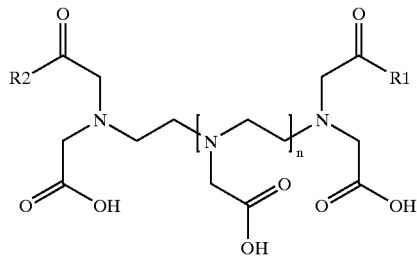

I wherein:

[\NA]$_n$ is a chelator selected from the group consisting of: diethylenetriaminepentaacetic acid (DTPA), wherein n=1 in Formula I, triethylenetetraaminehexaacetic acid (TTHA), wherein n=2 in Formula I, and a polycarboxylate derivative of DTPA or TTHA, which chelates a lanthanide metal cation;

R1 is a phenone; and

R2 is selected from the group consisting of: OH, $NH(CH_2)_nOH$, $NH(CH_2)_nNH_2$, $NH(CH_2)_nPhNH_2$, $NH(CH_2)_nPhOH$, $NHCH(CO_2H)CH_2PhNH_2$, $NH(CH_2)_nPhNCS$; wherein n is 1–6;

in fluorescence detection-based techniques or bioassays comprising the steps of:

a. labelling an aliquot comprising donor biomolecules selected from the group consisting of: peptides, proteins, deoxyribonucleic acids (DNAs), ribonucleic acids (RNAs), enzyme substrates, and ligand molecules with a compound of Formula I by a linking reaction with linker R2 to provide a labelled biomolecule assay sample;

b. adding a suitable amount of a suitable organic dye to the labelled biomolecule assay sample;

c. exciting the labelled biomolecule assay sample in a suitable fluorescence instrument to provide a fluorescence emission for quantitation.

3. A method according to claim 2 wherein said organic dye is selected from the group consisting of: rhodamine, allophycocyanin (APC) and indodicarbocyanin (CY-5).

4. A kit for fluorescence detection-based techniques or bioassays comprising:

a. a suitable amount of a compound of Formula I

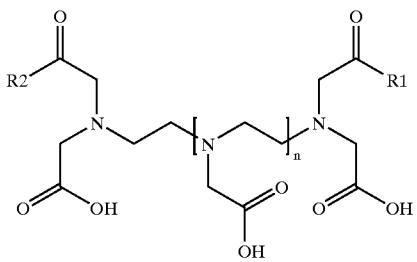

I wherein:

[\NA]$_n$ is a chelator selected from the group consisting of: diethylenetriaminepentaacetic acid (DTPA), wherein n=1 in Formula I, triethylenetetraaminehexaacetic acid (TTHA), wherein n=2 in Formula I, and a polycarboxylate derivative of DTPA or TTHA, wherein chelates a lanthanide metal cation;

R1 is a phenone; and

R2is selected from the group consisting of: OH, $NH(CH_2)_nOH$, $NH(CH_2)_nNH_2$, $NH(CH_2)_nPhNH_2$, $NH(CH_2)_nPhOH$, $NHCH(CO_2H)CH_2PhNH_2$, $NH(CH_2)_nPhNCS$; wherein n is 1–6; and b. a suitable amount of organic dye.

5. A kit according to claim 4 wherein said organic dye is selected from the group consisting of: rhodamine, allophycocyanin (APC) and indodicarbocyanin (CY-5).

6. A compound according to claim 1 wherein R3 and R4 are independently selected from the group consisting of: H, ON, $NH_2$, $COCH_3$, COPh, OPh, NHPh, CN, $NO_2$, $CO_2H$, and $CO_2CH_3$.

7. A compound according to claim 1 wherein [\NA]$_n$ is DTPA, wherein n=1 in Formula I.

8. A compound according to claim 1 wherein the lanthanide metal cation is selected from the group consisting of: Tb III, Eu III, Sm III, and Dy III.

9. A compound according to claim 8 wherein the lanthanide metal cation is selected from the group consisting of: Eu III or Tb III.

10. A method according to claim 2 wherein the phenone is selected from the group consisting of: aminoacetophenones (AAP), aminobenzophenones (ABP), aminofluorenones (AF), aminoxantones (AX), amino-azaxanthones (AAX), aminoanthraquinones (AAQ), and aminoacridones (AAC):

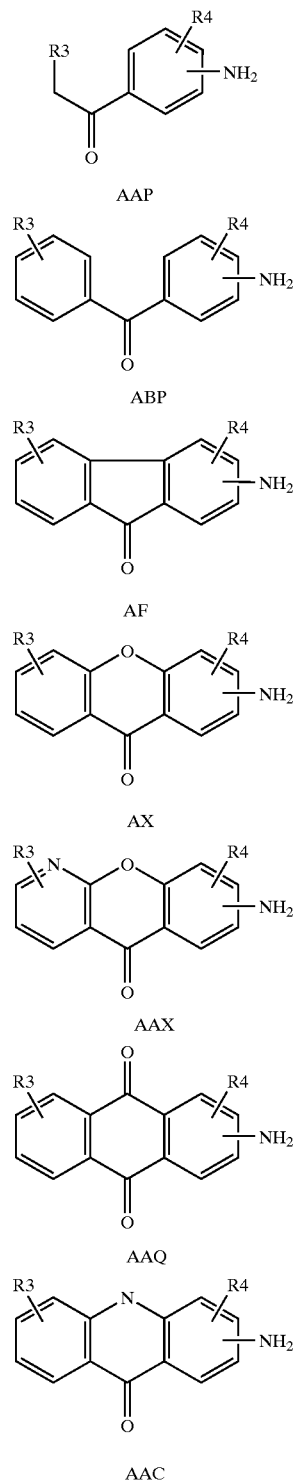

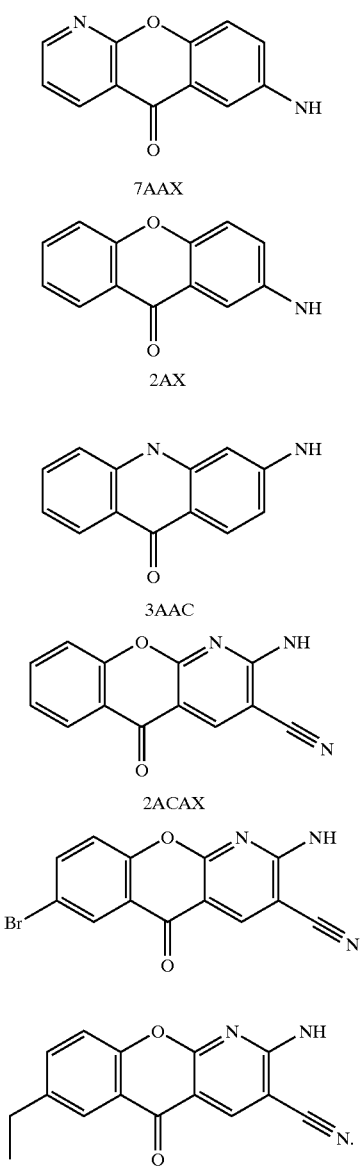

wherein R3 and R4 are independently selected from the group consisting of: H, OH, $NH_2$, $COCH_3$, COPh, OPh, NHPh, CN, $NO_2$, $CO_2H$, and $CO_2CH_3$.

11. A method according to claim 2 wherein the phenone is selected from the following group:

12. A method according to claim 2 wherein $[\backslash N\Lambda]_n$ is DTPA, wherein n=1 in Formula I.

13. A method according to claim 2 wherein the lanthanide metal cation is selected from the group consisting of: Tb III, Eu III, Sm III, and Dy III.

14. A method according to claim 13 wherein the lanthanide metal cation is selected from the group consisting of: Eu III or Tb III.

15. A kit according to claim 4 wherein the phenone is selected from the group consisting of: aminoacetophenones (AAP), aminobenzophenones (ABP), aminofluorenones (AF), aminoxantones (AX), amino-azaxanthones (AAX), aminoanthraquinones (AAQ), and aminoacridones (AAC):

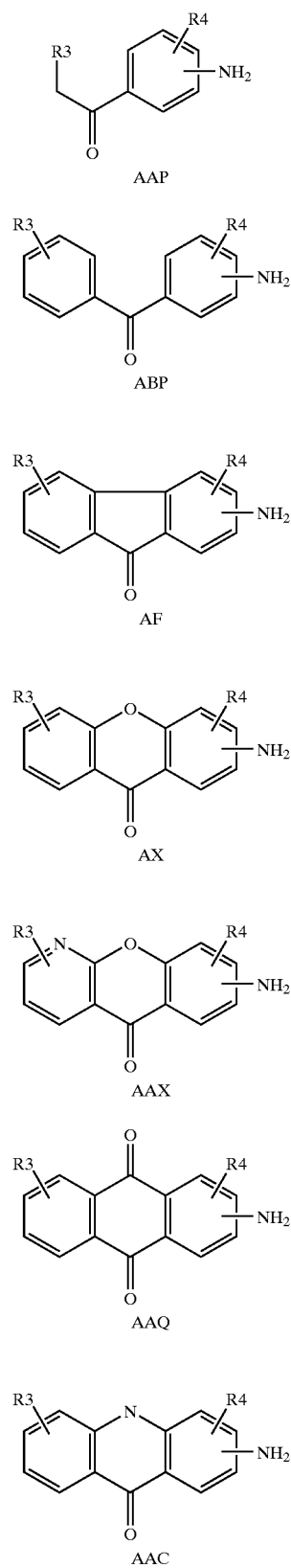

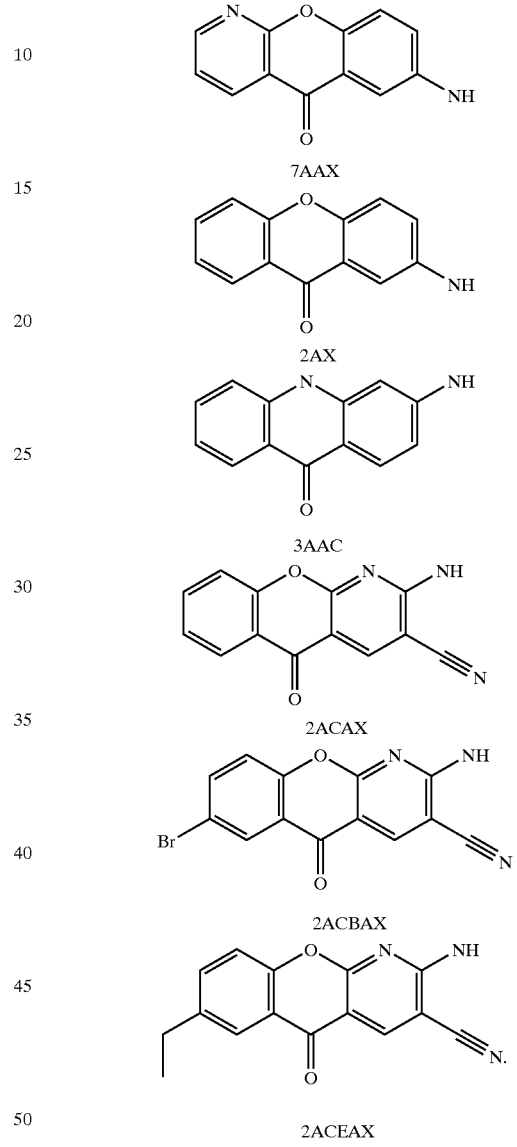

wherein R3 and R4 are independent selected from the group consisting of: H, OH, $NH_2$, $COCH_3$, COPh, OPh, NHPh, CN, $NO_2$, $CO_2H$, and $CO_2CH_3$.

16. A kit according to claim 4 wherein the phenone is selected from the following group:

17. A kit according to claim 4 wherein $[\backslash N\Lambda]_n$ is DTPA, wherein n=1 in Formula I.

18. A kit according to claim 4 wherein the lanthanide metal cation is selected from group consisting of: Tb III, Eu III, Sm III, and Dy III.

19. A kit according to claim 18 wherein the lanthanide metal cation is selected from group consisting of: Eu III or Tb III.

* * * * *